(12) United States Patent
Xu et al.

(10) Patent No.: US 12,082,865 B2
(45) Date of Patent: Sep. 10, 2024

(54) HIGH-FREQUENCY ELECTROTOME CONTROL SYSTEM AND CONTROL METHOD THEREOF

(71) Applicant: BEIJING SURGERII ROBOTICS COMPANY LIMITED, Beijing (CN)

(72) Inventors: Kai Xu, Beijing (CN); Aolin Tang, Beijing (CN)

(73) Assignee: BEIJING SURGERII ROBOTICS COMPANY LIMITED, Beijing (CN)

( * ) Notice: Subject to any disclaimer, the term of this patent is extended or adjusted under 35 U.S.C. 154(b) by 651 days.

(21) Appl. No.: 17/418,208

(22) PCT Filed: Dec. 27, 2019

(86) PCT No.: PCT/CN2019/129021
§ 371 (c)(1),
(2) Date: Jun. 24, 2021

(87) PCT Pub. No.: WO2020/135675
PCT Pub. Date: Jul. 2, 2020

(65) Prior Publication Data
US 2022/0061905 A1    Mar. 3, 2022

(30) Foreign Application Priority Data

Dec. 27, 2018    (CN) .......................... 201811610868.8

(51) Int. Cl.
*A61B 18/12* (2006.01)
*A61B 18/00* (2006.01)

(52) U.S. Cl.
CPC .... *A61B 18/12* (2013.01); *A61B 2018/00607* (2013.01); *A61B 2018/00642* (2013.01);
(Continued)

(58) Field of Classification Search
CPC . A61B 18/12; A61B 18/1206; A61B 18/1402; A61B 2018/00642; A61B 2018/00898; A61B 34/37; A61B 34/74
See application file for complete search history.

(56) References Cited

U.S. PATENT DOCUMENTS

| 2005/0165271 A1* | 7/2005 | Shioda .................. A61B 90/50 |
| | | 600/102 |
| 2009/0062786 A1 | 3/2009 | Garito et al. |

(Continued)

FOREIGN PATENT DOCUMENTS

| CN | 1957857 A | 5/2007 |
| CN | 103126763 A | 6/2013 |

(Continued)

OTHER PUBLICATIONS

Chinese Office Action in corresponding Chinese Application No. 2018116108688 dated Dec. 3, 2019 (3 pages).

(Continued)

*Primary Examiner* — Daniel W Fowler
(74) *Attorney, Agent, or Firm* — Bayes PLLC

(57) ABSTRACT

A high-frequency electrotome control system and a control method thereof are disclosed. The high-frequency electrotome control system includes an electrotome activation pedal, a master-slave control system, and a high-frequency electrotome activation hardware arbitration module. The high-frequency electrotome activation hardware arbitration module is connected with the electrotome activation pedal and configured to detect the state of the electrotome activation pedal. The high-frequency electrotome activation hardware arbitration module is connected with the master-slave control system and configured to activate an electrotome (Continued)

control output based on the state of the electrotome activation pedal and an electrotome control signal from the master-slave control system.

17 Claims, 7 Drawing Sheets

(52) U.S. Cl.
CPC .............. *A61B 2018/00898* (2013.01); *A61B 2018/00958* (2013.01)

(56) References Cited

U.S. PATENT DOCUMENTS

| | | | |
|---|---|---|---|
| 2011/0144636 A1 | 6/2011 | Alexander et al. | |
| 2013/0217967 A1 | 8/2013 | Mohr et al. | |
| 2014/0340796 A1 | 11/2014 | Sandhu et al. | |
| 2015/0105701 A1* | 4/2015 | Mayer | A61N 7/02 |
| | | | 601/3 |
| 2018/0049815 A1 | 2/2018 | Overmyer et al. | |
| 2019/0187741 A1* | 6/2019 | Walters | G05G 1/01 |
| 2020/0188048 A1* | 6/2020 | Vokrot | A61B 34/35 |

FOREIGN PATENT DOCUMENTS

| | | |
|---|---|---|
| CN | 105395254 A | 3/2016 |
| CN | 106154942 A | 11/2016 |
| CN | 205750623 U | 11/2016 |
| CN | 205831903 U | 12/2016 |
| CN | 206080684 U | 4/2017 |
| CN | 206729972 U | 12/2017 |
| CN | 208017573 U | 10/2018 |
| CN | 108814715 A | 11/2018 |
| CN | 109662776 A | 4/2019 |
| WO | 2009105488 A2 | 8/2009 |
| WO | 2018217522 A1 | 11/2018 |

OTHER PUBLICATIONS

International Search Report in corresponding PCT Application No. PCT/CN2019/129021 dated Mar. 26, 2020 (5 pages).

Extended European Search Report in corresponding European Application No. EP19904078 dated Jan. 17, 2022 (7 pages).

Office Action in related European Patent Application No. 19904078.3 dated Apr. 18, 2024 (6 pages).

* cited by examiner

HIGH-FREQUENCY ELECTROTOME CONTROL SYSTEM AND CONTROL METHOD THEREOF

CROSS-REFERENCE TO RELATED APPLICATIONS

This patent application is a U.S. National Phase of International Application No. PCT/CN2019/129021, filed on Dec. 27, 2019, which claims priority to Chinese Patent Application Ser. No. 20/181,1610868.8, filed on Dec. 27, 2018. The entire contents of each of the above-identified applications are incorporated herein by reference.

TECHNICAL FIELD

The disclosure relates to a high-frequency electrotome control system and a control method thereof, and relates to the technical field of medical instruments.

BACKGROUND

A high-frequency electrotome (also known as a high-frequency electrosurgical tool) is an electrosurgical instrument for replacing a traditional mechanical scalpel to cut tissues. Compared with a mechanical scalpel, high-frequency electrotome has the functions of cutting and blood coagulation, so that operation efficiency can be greatly improved, and operation risk can be reduced. High-frequency electrotome is easier to enter into different operation sites and applied to wide range of surgeries. In a robot-assisted minimally invasive surgical device (also referred to as a robotic-assisted minimally invasive surgical device), a high-frequency electrotome tool is generally installed to assist a surgeon to complete the operation with high efficiency. As shown in FIG. 1, an electrotome control module of a conventional high-frequency electrotome surgical device comprises a pedal, a high-frequency electrotome generator and a plurality of surgical tools. One high-frequency electrotome generator can be connected to the plurality of surgical tools at the same time. For each surgical tool, one foot pedal is used to control the surgical tool. For two surgical tools shown in FIG. 1, two pedals are required to be respectively connected to the high-frequency electrotome generator. The surgeon steps on the pedal 1, then high-frequency electrical energy is generated on the corresponding operation tool 1. Stepping on the pedal 2 generates high-frequency power on the surgical tool 2. But when more surgical tools are connected, unavoidably, the surgeon may make mistakes when busy and step on a wrong pedal. In the prior art, the electrotome can be triggered in a wireless communication mode, which is only a derivative form of the control mode of the traditional high-frequency electrotome surgical device shown in FIG. 1. Moreover, the design of a wireless communication mechanism needs caution, and should meet relevant regulatory requirements and reliability requirements.

In a robot-assisted minimally invasive surgical device, a high-frequency electrotome control mode different from the conventional control mode is shown in FIG. 2 (currently the world's most successfully commercialized da Vinci surgical machine): the surgeon sits beside a console, and operates a main controller to manipulate robot surgical tools at a slave control terminal of the robot to perform an operation. When the high-energy electrotome function needs to be activated, the surgeon steps on the corresponding pedal. After the control system detects the pedal closing signal (in FIG. 2, the right pedal is used as a function control pedal for the electrotome), according to a serial number and type of currently operated robot surgical tool, a corresponding control signal is sent to the high-frequency electrotome generator at the slave control terminal of the robot, to activate the electroexcision or electrocoagulation function of the currently operated robot surgical tool. From comparison of FIG. 1 and FIG. 2, compared with the traditional control process of high-frequency electrotome, the robot-assisted minimally invasive surgical device has an intervention of master-slave control system. The pedal of the surgeon console is no longer directly connected to the high-frequency electrotome generator to control the high-frequency electrotome generator to produce corresponding high-frequency energy output, but is first connected to the control system with decision and processing of corresponding software. Then, a signal is output to drive the high-frequency electrotome generator to output high-frequency energy to the currently-controlled robot surgical tool. As such, the three robot surgical tools shown in FIG. 2 do not require three pedals to control their electroexcision and electrocoagulation functions, respectively. The surgeon can control different robot surgical tools through the same pedal to realize electric electroexcision and electrocoagulation at different moments. Compared with the traditional high-frequency electrotome surgical device control mode, the method saves the hardware cost, and the surgeon does not need to remember the corresponding relation between the pedals and the surgical tools, so that the control is simpler and more intuitive.

However, the above method brings advantages and corresponding risks. If the associated control software fails, the high-frequency electrotome generator may be caused to output high-frequency electrical energy to the wrong robot surgical tool. Or when the surgeon does not step on the pedal, the high-frequency electrotome generator is controlled to output high-frequency electrical energy to the surgical tool. The consequence may be very serious. As previously described, there are typically multiple electrotome surgical tools in robot-assisted minimally invasive surgical device. To simplify the operation, improve operation efficiency, software logic processing is introduced into robot-assisted minimally invasive surgery device to realize intelligent control of the high-frequency electrotome. But because high-frequency electrical energy output control is completely based on software logic decision, the method introduces a new risk that if related software runs incorrectly, high-frequency electrical energy output can be caused in a wrong way, and serious death of a patient can be caused.

SUMMARY

In view of the above problems, an objective of the present disclosure is to provide a high-frequency electrotome control system capable of avoiding wrong electrotome output caused by software faults and a control method thereof.

Thus, the present disclosure discloses the following technical solutions:

In the first aspect, present disclosure provides a high-frequency electrotome control system, comprising an electrotome activation pedal, a master-slave control system and a high-frequency electrotome activation hardware arbitration module. The electrotome activation pedal is connected with the master-slave control system and the high-frequency electrotome activation hardware arbitration module, and the master-slave control system and the high-frequency electrotome activation hardware arbitration module are capable of detecting a state of the electrotome activation pedal. The high-frequency electrotome activation hardware arbitration module comprises a logic OR circuit, a plurality of logic AND circuits and a plurality of switch elements. The logic OR circuit is to perform logic OR operation on a contact signal of the electrotome activation pedal. A hardware control signal outputted by the logic OR circuit is sent to the master-slave control system for feedback, and another hardware control signal outputted by the logic OR circuit is performed a logic AND operation with a plurality of software control signals sent by the master-slave control system, respectively, A result of the logic AND operation is used to control a switching action of the switch element connected with a high-frequency electrotome generator.

In addition, the master-slave control system further receives an output terminal signal of the switch element as a back-collected signal to determine whether the switch element normally perform a switching action.

In addition, the high-frequency electrotome activation hardware arbitration module further comprises a plurality of standby switches, and the master-slave control system further outputs a plurality of emergency control signals to cut off the standby switches arranged between the switch elements and the high-frequency electrotome generator so as to ensure that wrong output signal is cut off.

In addition, the electrotome activation pedal comprises a left-hand tool electroexcision activation pedal, a left-hand tool electrocoagulation activation pedal, a right-hand tool electroexcision activation pedal and a right-hand tool electrocoagulation activation pedal. Each of the pedals includes two independent contacts. One of the two contacts of each pedal is connected with the master-slave control system. The other one of the two contacts of each pedal is connected with an input terminal of the logic OR circuit. A hardware control signal of the logic OR circuit is fed back to the master-slave control system, and another hardware control signal and each software control signal output by the control module in the master-slave control system are subjected to logic AND operation.

In a second aspect, present disclosure provides a control method based on the high-frequency electrotome control system comprising:

S1. checking whether each output path of the high-frequency electrotome activation hardware arbitration module is in an off state through a back-collected signal after the master-slave control system finishes initialization, and if yes, proceeding to S2;

S2. determining, by the master-slave control system, whether an electrotome activation pedal is pressed by detecting the pedal function signal or the hardware control signal output by the high-frequency electrotome activation hardware arbitration module. If both the pedal function signal and the hardware control signal output by the high-frequency electrotome activation hardware arbitration module are not detected, it is determined that no electrotome activation pedal is pressed. When the master-slave control system detects a certain pedal function signal or a hardware control signal outputted by the high-frequency electrotome activation hardware arbitration module, the master-slave control system determines whether both signals are detected. If not both signals are detected, an electrotome activation pedal contact is determined to fail. If both signal are detected, the triggering is determined to be valid, and the master-slave control system outputs corresponding software control signal according to the detected pedal function signal and surgical tool currently to be controlled;

S3. performing, by the logic AND circuit of the high-frequency electrotome activation hardware arbitration module, logic AND operation on the hardware control signal and the software control signal to drive corresponding switch element to close and conduct, so as to activate corresponding electroexcision or electrocoagulation function of the high-frequency electrotome generator, and the master-slave control system determines whether corresponding output path of the high-frequency electrotome activation hardware arbitration module is normal through the back-collected signal. If the abnormality is detected, corresponding erroneous output path is cut off through emergency control signal;

S4. before the electrotome activation pedal is released, continuously outputting, by the master-slave control system, software control signal, and determining whether corresponding output path of the high-frequency electrotome activation hardware arbitration module is normal through the back-collected signal. When the electrotome activation pedal is released, the master-slave control system closes the software control signal, and determines whether the corresponding output path of the high-frequency electrotome activation hardware arbitration module is normally closed through the back-collected signal, and continues to detect and waits for next pressing of the electrotome activation pedal;

In addition, the user can select to enter a fault-tolerant control mode if the master-slave control system detects that a certain output path of the high-frequency electrotome activation hardware arbitration module should not be in an activated state but is actually activated.

In addition, control flow of the fault-tolerant control mode comprises: detecting whether a pedal is pressed by detecting a pedal function signal or a hardware control signal outputted by the high-frequency electrotome activation hardware arbitration module, if both the pedal function signal and the hardware control signal fed back by the high-frequency electrotome activation hardware arbitration module are not detected, it is determined that no electrotome activation pedal is pressed, and the master-slave control system continues to detect whether the pedal is pressed; when the electrotome activation pedal is pressed, determining, by the master-slave control system, whether both the pedal function signal and the hardware control signal are detected, and if not both the pedal function signal and the hardware control signal are detected, an electrotome activation pedal contact is determined to fail; if both the pedal function signal and the hardware control signal are detected, the master-slave control system determines that the triggering is valid, and outputs a corresponding software control signal according to the detected pedal function signal and the current surgical tool; determining, by the master-slave control system, whether an output path currently required to be activated is an erroneous output path, if it is not the output path with detected failure, corresponding logic AND circuit on the high-frequency electrotome activation hardware arbitration module drives corresponding switch element to switch, if it is the output path with detected failure, the standby switch is closed, the corresponding logic AND circuit on the high-frequency electrotome activation hardware arbitration module drives the corresponding switch element to switch until the electrotome activation pedal is released, the fault-tolerant control is ended, and if the failure still exists, the fault-tolerant control mode is entered again.

Present disclosure discloses above technical solutions which can bring following advantages: 1. in addition to introducing software logic processing to realize intelligent control of the high-frequency electrotome, present disclosure also introduces an independent hardware logic loop to ensure correctness of the final output control signal, which can improve the reliability of the system, avoid casualties caused by wrong electrotome output due to control software failure, and further improve the safety and reliability of the robot-assisted surgery, 2. The control method provided by the disclosure can realize fault-tolerant control while detecting a fault and providing an alarm, and ensure that an electrotome function can still be used under the condition of faults so as to cope with special emergencies.

DETAILED DESCRIPTION OF EMBODIMENTS

In order to make objectives, technical solutions and advantages of embodiments of the disclosure clearer, with reference to accompanying drawings of embodiments of the present disclosure, technical solutions in the embodiments of the disclosure is clearly and completely described. Obviously, the embodiments described are part of, rather than all of, embodiments of the present disclosure. Based on the embodiments of the present disclosure, all other embodiments obtained by those of ordinary skill in the art without inventive work fall within the scope of the present disclosure.

Figure 1:
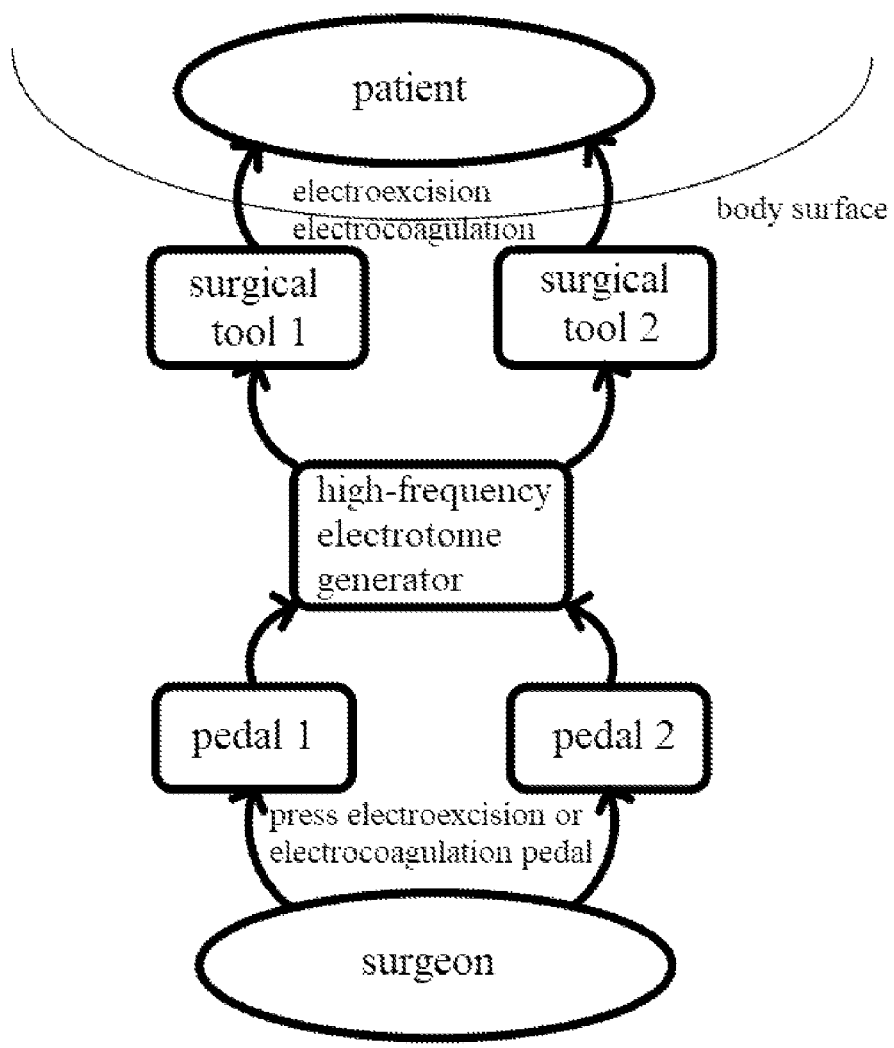
FIG. 1 is a schematic control flow diagram of a conventional high-frequency electrotome surgical device.
Figure 2A:
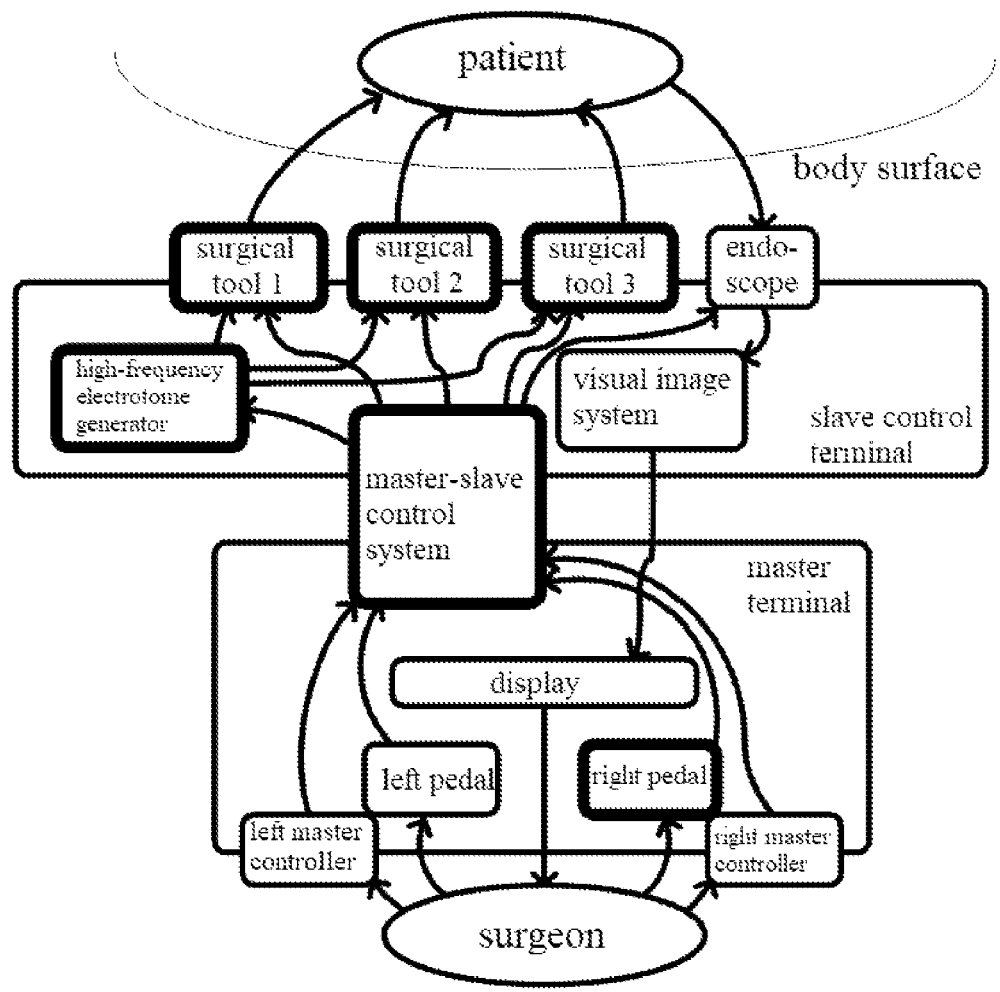
FIG. 2(a) is a high-frequency electrotome integration in a conventional robot-assisted minimally invasive surgical device.
Figure 2B:
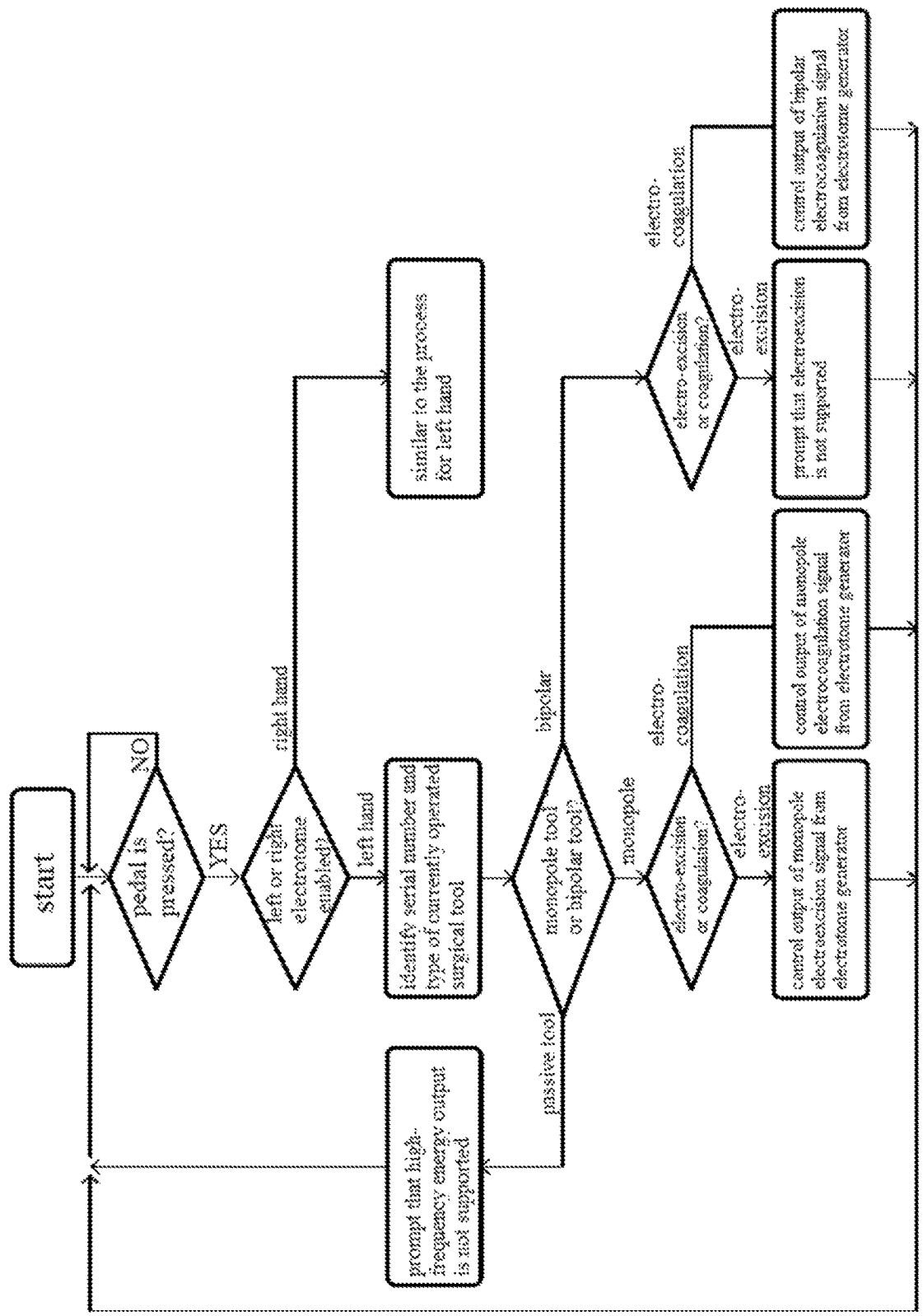
FIG. 2(b) is a schematic control flow diagram of a conventional robot-assisted minimally invasive surgical device.
Figure 3:
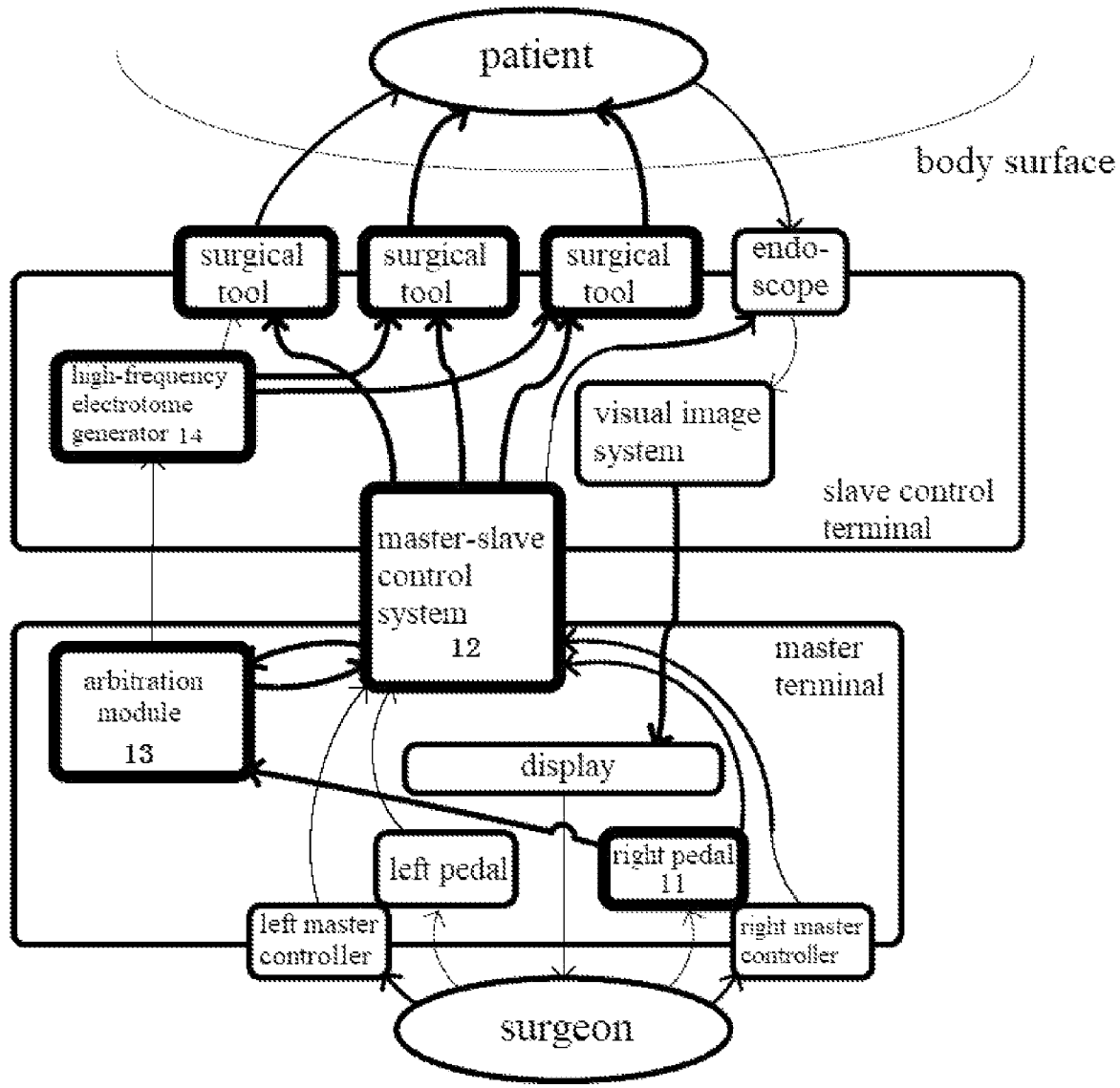
FIG. 3 is a control logic block diagram of a high-frequency electrotome control system of the present disclosure.

As shown in FIG. 3, a high-frequency electrotome control system provided by the present disclosure includes an electrotome activation pedal 11, a master-slave control system 12, a high-frequency electrotome activation hardware arbitration module 13, a high-frequency electrotome generator 14 and a corresponding surgical tool.

The electrotome activation pedal 11 (in FIG. 3, a right pedal is still used as the electrotome activation pedal, and a left pedal controls other functions) is connected with both the master-slave control system 12 and the high-frequency electrotome activation hardware arbitration module 13. Then, the master-slave control system 12 and the high-frequency electrotome activation hardware arbitration module 13 can detect an on or off state of the electrotome activation pedal 11

An output of the high-frequency electrotome activation hardware arbitration module 13 is connected with the high-frequency electrotome generator 14 to activate the high-frequency electrotome generator 14 to output high-frequency electrical energy. Then the high-frequency electrotome generator 14 is connected with each robot surgical tool, and transmits electrical energy to each surgical tool, so that electroexcision or electrocoagulation function can be realized.

The high-frequency electrotome activation hardware arbitration module 13 can be in bidirectional communication with the master-slave control system 12. An electrotome control output signal of the master-slave control system 12 is no longer directly connected with the high-frequency electrotome generator 14, but connected with the high-frequency electrotome activation hardware arbitration module 13. The high-frequency electrotome activation hardware arbitration module 13 can activate corresponding electrotome control output path after comprehensively considering various signals. In addition, the high-frequency electrotome activation hardware arbitration module 13 can feedback logic decision result to the master-slave control system 12. If any abnormality occurs, the master-slave control system 12 can trigger a corresponding alarm mechanism.

Figure 4:
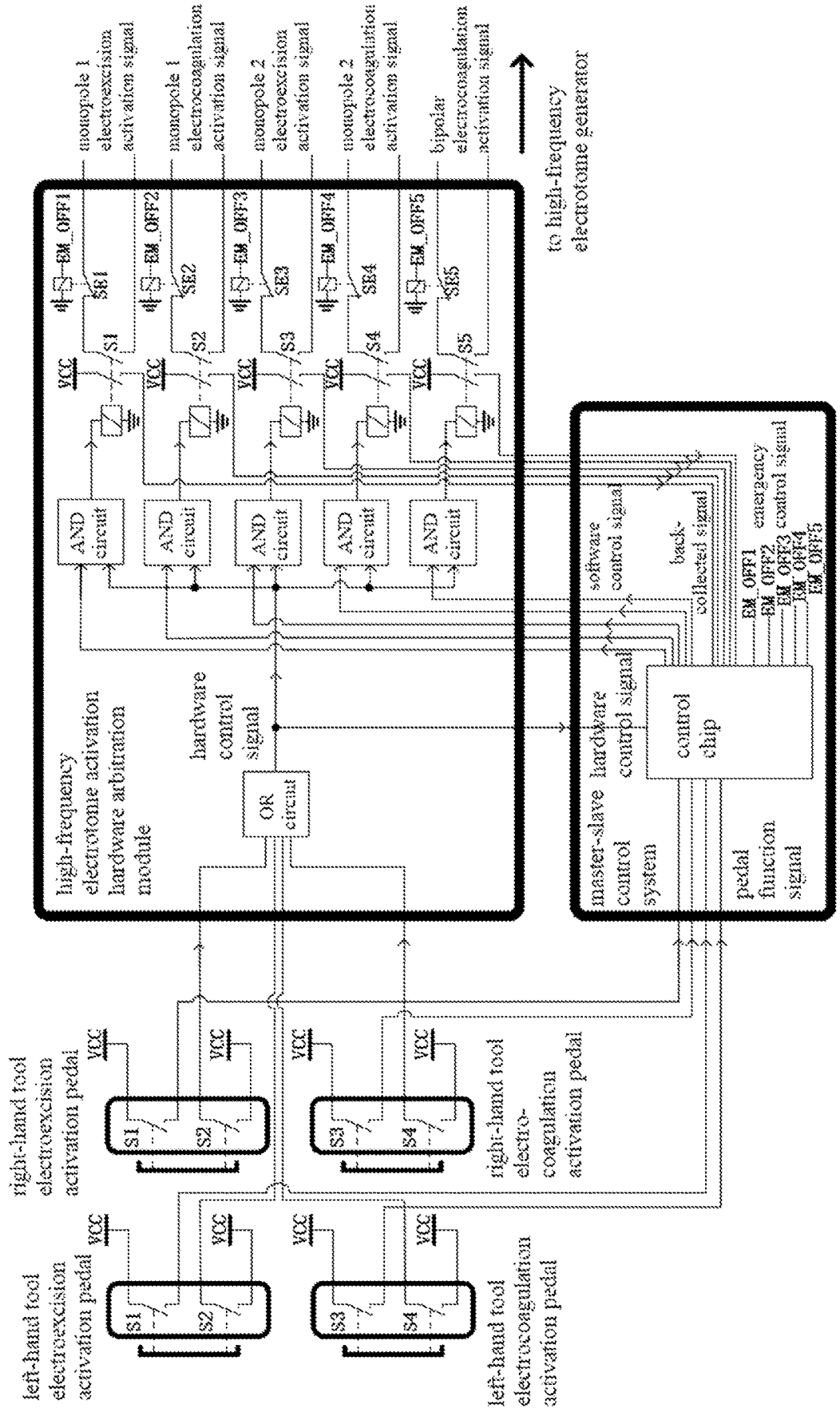
FIG. 4 is an implementation of a high-frequency electrotome activation hardware arbitration module according to an embodiment of the present disclosure.

As shown in FIG. 4, the high-frequency electrotome activation hardware arbitration module 13 includes a logic OR circuit 131, a plurality of logic AND circuits 132, and a plurality of switch elements. Logic OR circuitry 131 is used to perform logic OR operation on contact signals of the electrotome activation pedal 11. A hardware control signal output by logic OR circuit 131 is sent to master-slave control system 12 for feedback, an another hardware control signal outputted by logic OR circuit 131 is used to perform logic AND operations with a plurality of software control signals outputted by master-slave control system 12. Results of the logical AND operations are used to control respective switch elements to close or open. Outputs of respective switch elements are connected to respective input control interfaces of the high-frequency electrotome generator 14. In addition, the high-frequency electrotome activation hardware arbitration module 13 also includes a plurality of standby switches. A control module of the master-slave control system 12 can acquire a pedal contact signal and detect a state of each pedal. The control module outputs a plurality of software control signals according to the surgical tool to be controlled. The control module also receives a signal output by the switch element as a back-collected signal which can be used to determine whether the switch element normally perform switching action or not. The control module can also output emergency control signals EM_OFF1-EM_OFF5 to cut off the standby switch so as to ensure that the wrong output signal is cut off.

Figure 5:
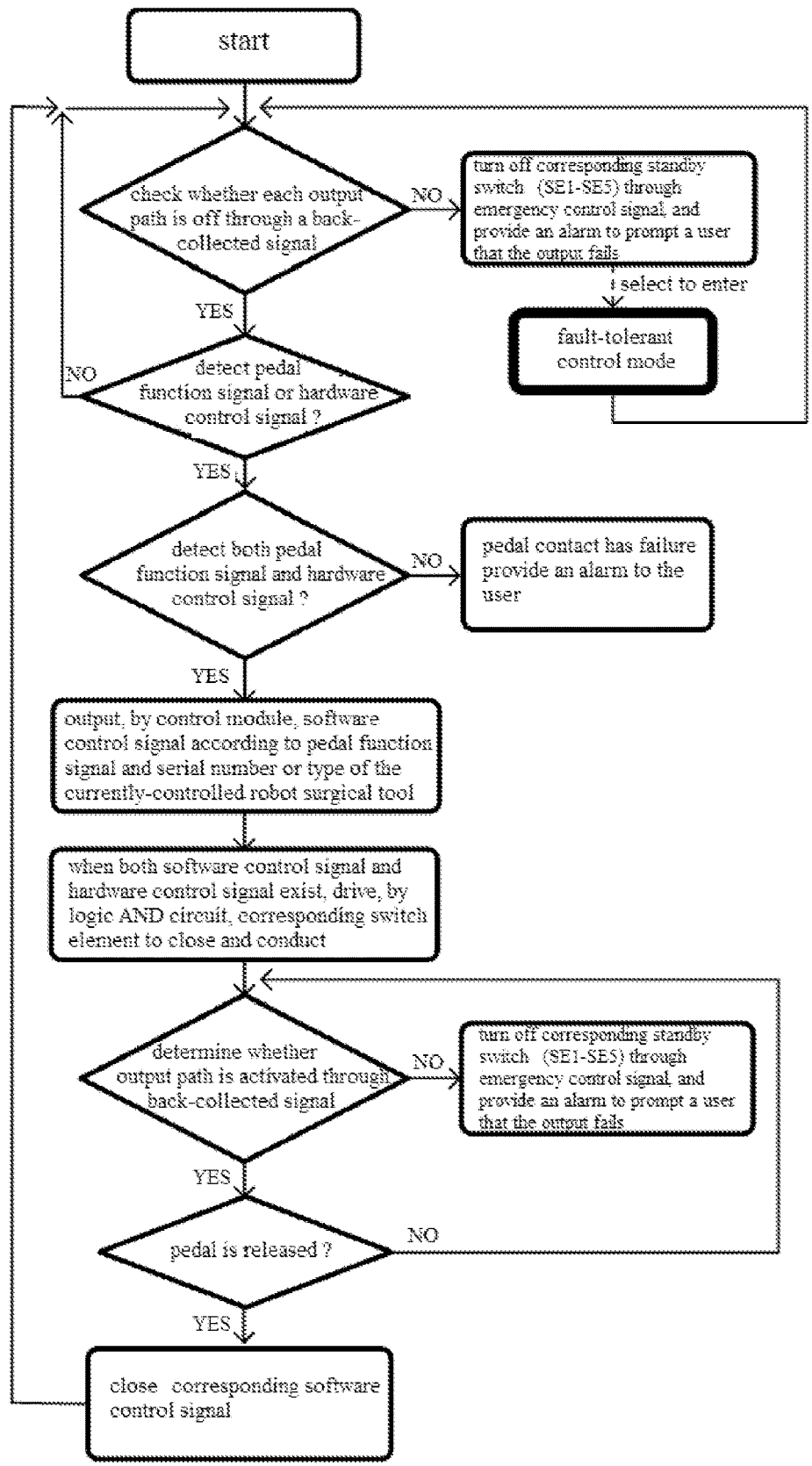
FIG. 5 is a flow diagram of a high-frequency electrotome control method of the present disclosure.

In an embodiment, as shown in FIG. 4, this embodiment employs four pedals (a left hand tool electroexcision activation pedal, a left hand tool electrocoagulation activation pedal, a right hand tool electroexcision activation pedal and a right hand tool electrocoagulation activation pedal). The four pedals are divided into two groups for activating the electroexcision or electrocoagulation function of the tools controlled by the left hand and the right hand, respectively. Each pedal includes two independent contacts S1 and S2. When the pedal is stepped down, the two contacts S1 and S2 can be closed. One of the two contacts of each pedal is connected with the control module in the master-slave control system, so that the control module can detect a state of each pedal. The other contact of the two contacts of each pedal is connected with an input terminal of the logic OR circuit 131 of the high-frequency electrotome activation hardware arbitration module 13. Logic OR operation is performed on four contact signals. A hardware control signal of the logic OR circuit 131 is fed back to the control module of the master-slave control system, another hardware control signal and each software control signal output by the control module in the master-slave control system 12 are respectively subjected to logic AND operation (this embodiment takes five output as an example, because currently many electrotome generators simultaneously support at most two monopole tools and one bipolar tool, requiring five control inputs. By way of example, specific number can be selected according to actual requirement). Output signals of logic AND operations can be used to control corresponding switch elements (for example, relays in this embodiment) K1-K5 to close or open. Each switch element (K1-K5) is respectively connected with the corresponding input control interface of the high-frequency electrotome generator 14. Therefore, activation of electroexcision or electrocoagulation function is no longer simply determined by the software control signal of the master-slave control system 12. When both the software output signal and the hardware signal (the output signal of the logic OR circuit) are activated, the corresponding electrotome function can be triggered. Thus, even if the software fails, the function of the electrotome cannot be triggered by mistake by disconnecting the hardware signal. In order to prevent an erroneous electrotome activation signal from being generated due to failure of the corresponding switch element, the output part of the switch element is designed with a back-collected signal. The back-collected signal is fed back to the control module of the master-slave control system 12. The control module can detect whether the switch element normally completes switching action or not. If the switch element fails, the control module can cut off standby switches SE1-SE5 connected between the switch element and the corresponding input control interface of the high-frequency electrotome generator through emergency control signals EM_OFF1-EM_OFF5 to ensure that wrong output signals are cut off As shown in FIG. 5, present disclosure provides a method of the high-frequency electrotome control system including the following process.

After the control module of the master-slave control system 12 finishes initialization and starts normal work, whether each output path of the high-frequency electrotome activation hardware arbitration module 13 is in an off state is checked through a back-collected signal.

If any one of the output paths is detected to have been activated, the master-slave control system 12 turns off the corresponding standby switches (SE1-SE5) through emergency control signals, so as to cut off the wrong output path. An alarm can be provided to prompt a user that the electrotome function fails. The user can select to stop operation and remove the failure. The user can also select to enter into fault-tolerant control mode so as to cope with a case that the electrotome function still needs to be used under the emergency condition.

If the output paths are normal, the control module of the master-slave control system 12 detects whether a pedal is pressed by detecting a pedal function signal or a hardware control signal outputted by the high-frequency electrotome activation hardware arbitration module 13. If neither the pedal function signal nor the hardware control signal fed back by the high-frequency electrotome activation hardware arbitration module 13 is detected, then no pedal is considered to be pressed. When a pedal is pressed at a certain time, the control module of the master-slave control system 12 detects the function signal of the pedal or the hardware control signal fed back by the high-frequency electrotome activation hardware arbitration module 13. Then, the control module can determine whether both signals are detected. If not, it is determined that a pedal contact has failure. The control module provides an alarm to the user. If both signals are detected, the control module determines that the triggering is valid and outputs corresponding software control signal according to the detected pedal function signal and a serial number or type of the currently-controlled robot surgical tool. Different pedals represent different functions, and the pedal function signal refer to a signal sent by a pedal when being pressed down.

Because both the software control signal and the hardware control signal exist, the corresponding logic AND circuit 132 on the high-frequency electrotome activation hardware arbitration module 13 can output an effective high level to drive a corresponding switch element to close and conduct, thereby activating the corresponding electroexcision or electrocoagulation function of the high-frequency electrotome generator 14. The control module determines whether the corresponding output path of the high-frequency electrotome activation hardware arbitration module is actually in an activated state by the back-collected signal. If an abnormality is detected (the output path which should be in the activated state is not activated, or the output path which should not in the activated state is activated), the control module cuts off the corresponding erroneous output path through the emergency control signal, and sends an alarm prompt to the user.

Before the pedal is released (either the functional signal of the pedal or the hardware control signal fed back by the high-frequency electrotome activation hardware arbitration module 13 disappears), the control module can continuously output software control signal, and determine whether the corresponding output path of the high-frequency electrotome activation hardware arbitration module 13 is normal or not through the back-collected signal. When the pedal is released, the control module closes the software control signal, determines whether the corresponding output path of the high-frequency electrotome activation hardware arbitration module 13 is normally closed or not through the back-collected signal, then continues to detect and waits for a next pressing of the pedal.

Moreover, if the control module of the master-slave control system 12 detects that a certain output path of the high-frequency electrotome activation hardware arbitration module 13 should not be in an activated state but is actually activated, the master-slave control system 12 can turn off the corresponding standby switch (SE1-SE5) through emergency control signal so as to turn off the wrong output path. The user can select to enter the fault-tolerant control mode to cope with a case that the electrotome function is still needed in emergency condition.

Figure 6:
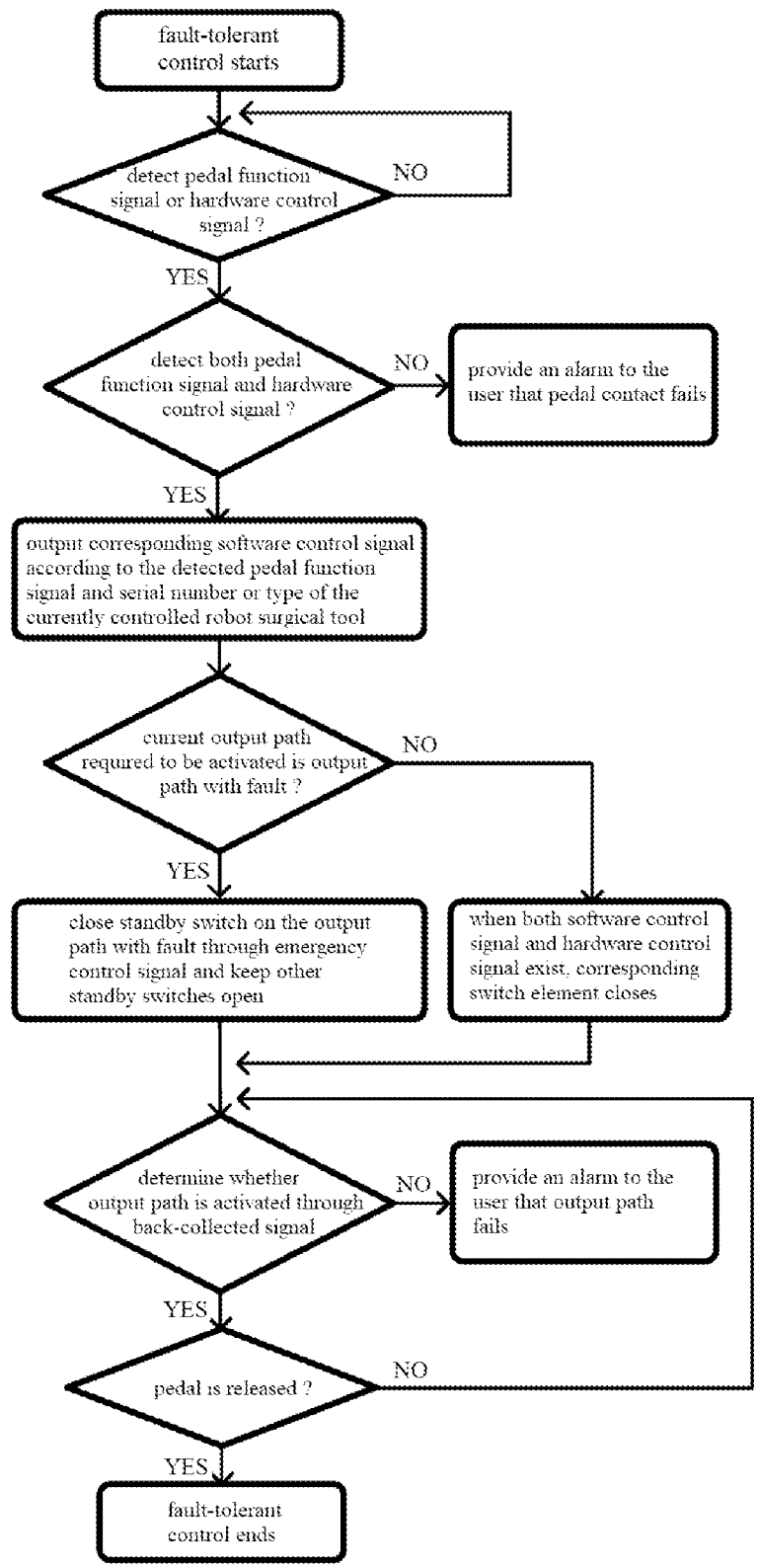
FIG. 6 is a schematic diagram of a fault-tolerant control process of a high-frequency electrotome of the present disclosure

As shown in FIG. 6, the fault-tolerant control mode is similar to a normal control flow. The fault-tolerant control starts.

Firstly, whether a pedal is pressed or not is detected by detecting a pedal function signal or a hardware control signal fed back by a high-frequency electrotome activation hardware arbitration module 13. If the pedal function signal and the hardware control signal fed back by the high-frequency electrotome activation hardware arbitration module 13 are not detected, no pedal is considered to be pressed down, and the control module continues to periodically detect whether the pedal is stepped down or not.

When the pedal is pressed (for example, the control module of the master-slave control system 12 detects a function signal of a certain pedal or a hardware control signal fed back by the high-frequency electrotome activation hardware arbitration module 13), the control module continues to determine whether both signals are detected. If not, it is determined that a pedal contact fails, and the control module can provide an alai to the user. If both signals are detected, the control module determines that the trigger is valid, and outputs a corresponding software control signal according to the detected pedal function signal and the serial number or type of the currently controlled robot surgical tool.

Unlike normal control process, in the fault-tolerant control, the control module also determines whether the current output path required to be activated is an output path with fault. If it is not the output path where the fault is detected, then it is similar to normal control process. Because both the software control signal and the hardware control signal exist, the corresponding logic AND circuit on the high-frequency electrotome activation hardware arbitration module 13 can output effective high level to drive the corresponding switch elements to close and conduct, so as to activate the corresponding electrocoagulation function of the high-frequency electrotome generator. But if the output path required to be activated is the output path with fault, since the control system has previously switched off the corresponding standby switch through the emergency control signal, the standby switch needs to be closed again to output the corresponding electrotome function activation signal. Then, the fault-tolerant control process is similar to the normal control process until the pedal is released and the fault-tolerant control is ended. If the fault still exists, the system automatically enters the fault-tolerant control again.

In summary, the present disclosure introduces an additional high-frequency electrotome activation hardware arbitration module 13 into the system. Control software failure can be effectively prevented from directly causing wrong electrotome output. A certain degree of fault-tolerant control can be realized. The robustness of the system is improved. A user can still continue to use the electrotome function under the condition of certain failure so as to cope with some special emergencies.

Based on the disclosure and teaching of the foregoing description, those skilled in the related art can also make appropriate changes and modifications to the foregoing embodiments. Therefore, the present disclosure is not limited to the specific embodiments disclosed and described above, and some modifications and changes to the present disclosure should also fall within the protection scope of the claims of the present disclosure. In addition, although some specific terms are used in this disclosure, these terms are only for convenience of description and do not constitute any limitation to the present disclosure.

The invention claimed is:

1. A high-frequency electrotome control system, comprising:
an electrotome activation pedal;
a master-slave control system connected with the electrotome activation pedal and configured to detect a state of the electrotome activation pedal; and
a high-frequency electrotome activation hardware arbitration module connected with the electrotome activation pedal and configured to detect the state of the electrotome activation pedal, the high-frequency electrotome activation hardware arbitration module being connected with the master-slave control system and configured to activate an electrotome control output based on the state of the electrotome activation pedal and an electrotome control signal from the master-slave control system;
wherein the high-frequency electrotome activation hardware arbitration module comprises:
a logic OR circuit comprising an input terminal and an output terminal, the input terminal being connected with the electrotome activation pedal;
a plurality of logic AND circuits each comprising a first input terminal and a second input terminal, the first input terminal being connected with the output terminal of the logic OR circuit and the second input terminal being connected with the master-slave control system; and
a plurality of switch elements connected with the plurality of logic AND circuits, respectively, wherein the plurality of logic AND circuits are configured to control the plurality of switch elements to activate the electrotome control output.

2. The high-frequency electrotome control system of claim 1, wherein the high-frequency electrotome activation hardware arbitration module is configured to feed back the activation of the electrotome control output to the master-slave control system.

3. The high-frequency electrotome control system of claim 1, wherein the master-slave control system is configured to trigger an alarm mechanism in response to an occurrence of an abnormality in the activation of the electrotome control output.

4. The high-frequency electrotome control system of claim 1, wherein the master-slave control system is connected with the output terminal of the logic OR circuit and configured to output the electrotome control signal based on a pedal function signal of the electrotome activation pedal and a hardware control signal from the logic OR circuit.

5. The high-frequency electrotome control system of claim 4, wherein the master-slave control system is configured to output an alarm in response to detection of either the pedal function signal or the hardware control signal, but not both.

6. The high-frequency electrotome control system of claim 1, wherein the master-slave control system is further configured to receive an output terminal signal of at least one of the plurality of switch elements as a back-collected signal to determine whether the at least one of the plurality of switch elements normally performs a switching action.

7. The high-frequency electrotome control system of claim 6, wherein:
the high-frequency electrotome activation hardware arbitration module further comprises a plurality of standby switches arranged between the plurality of switch elements and a high-frequency electrotome generator; and
the master-slave control system is further configured to output a first emergency control signal to cut off a first standby switch in response to a determination that a first switch element connected with the first standby switch abnormally performs a switching action.

8. The high-frequency electrotome control system of claim 7, wherein the master-slave control system is configured to enter, in response to the determination that the first switch element abnormally performs the switching action, a fault-tolerant control mode where the master-slave control system is configured to output a second emergency control signal to control the first standby switch based on a pedal function signal of the electrotome activation pedal and a hardware control signal from the logic OR circuit.

9. The high-frequency electrotome control system of claim 1, wherein the electrotome activation pedal comprises a left-hand tool electroexcision activation pedal, a left-hand tool electrocoagulation activation pedal, a right-hand tool electroexcision activation pedal, and a right-hand tool electrocoagulation activation pedal.

10. The high-frequency electrotome control system of claim 1, wherein the electrotome activation pedal comprises a first independent contact connected with the master-slave control system and a second independent contact connected with the high-frequency electrotome activation hardware arbitration module.

11. A control method, performed by a high-frequency electrotome control system, the high-frequency electrotome control system comprising an electrotome activation pedal, a master-slave control system connected with the electrotome activation pedal, and a high-frequency electrotome activation hardware arbitration module connected with the electrotome activation pedal and the master-slave control system, the control method comprising:
　determining, by the master-slave control system, whether both a pedal function signal from the electrotome activation pedal and a hardware control signal output by the high-frequency electrotome activation hardware arbitration module are detected;
　in response to a determination that both the pedal function signal and the hardware control signal are detected, outputting, by the master-slave control system, a software control signal according to the detected pedal function signal and a surgical tool to be controlled;
　activating, by the high-frequency electrotome activation hardware arbitration module, an electrotome control output based on the hardware control signal and the software control signal;
　determining, by the master-slave control system, whether a first output path of the high-frequency electrotome activation hardware arbitration module ought not be in an activated state is in fact activated;
　in response to a determination that the first output path is in fact activated, cutting off, by the master-slave control system, a first standby switch through a first emergency control signal, and entering a fault-tolerant control mode where the master-slave control system is configured to output a second emergency control signal to control the first standby switch based on the pedal function signal of the electrotome activation pedal and the hardware control signal from the high-frequency electrotome activation hardware arbitration module; and
　after entering the fault-tolerant control mode:
　　determining, by the master-slave control system, whether an output path currently required to be activated is the first output path; and
　　in response to a determination that the output path currently required to be activated is the first output path, outputting, by the master-slave control system, the second emergency control signal to switch on the first standby switch.

12. The control method of claim 11, comprising:
performing, by a logic AND circuit of the high-frequency electrotome activation hardware arbitration module, a logic AND operation on the hardware control signal and the software control signal to switch on a corresponding switch element.

13. The control method of claim 11, comprising:
determining, by the master-slave control system, whether an output path of the high-frequency electrotome activation hardware arbitration module is abnormal based on a back-collected signal; and
in response to a detection of an abnormality, cutting off, by the master-slave control system, a corresponding standby switch through an emergency control signal.

14. The control method of claim 11, comprising:
determining, by the master-slave control system, whether an output path of the high-frequency electrotome activation hardware arbitration module is normal based on a back-collected signal.

15. The control method of claim 11, further comprising:
in response to a failure to detect both the pedal function signal and the hardware control signal, determining, by the master-slave control system, that the electrotome activation pedal fails.

16. The control method of claim 11, further comprising, after entering the fault-tolerant control mode:
in response to a determination that the output path currently required to be activated is not the first output path, driving, by the high-frequency electrotome activation hardware arbitration module, a switch element corresponding to the output path currently required to be activated to switch on.

17. The control method of claim 11, further comprising, after entering the fault-tolerant control mode:
in response to a release of the electrotome activation pedal, exiting the fault-tolerant control mode.

* * * * *